United States Patent
Tamura

(10) Patent No.: US 10,117,628 B2
(45) Date of Patent: Nov. 6, 2018

(54) PHOTON COUNTING APPARATUS

(71) Applicant: Toshiba Medical Systems Corporation, Otawara-shi (JP)

(72) Inventor: Emi Tamura, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 297 days.

(21) Appl. No.: 14/870,386

(22) Filed: Sep. 30, 2015

(65) Prior Publication Data

US 2016/0095561 A1    Apr. 7, 2016

(30) Foreign Application Priority Data

Oct. 1, 2014  (JP) ................................. 2014-203368
Sep. 29, 2015  (JP) ................................. 2015-191306

(51) Int. Cl.
    *A61B 6/03*    (2006.01)
    *A61B 6/00*    (2006.01)

(52) U.S. Cl.
CPC .............. *A61B 6/482* (2013.01); *A61B 6/032* (2013.01); *A61B 6/4035* (2013.01); *A61B 6/42* (2013.01); *A61B 6/4233* (2013.01); *A61B 6/4241* (2013.01); *A61B 6/5205* (2013.01)

(58) Field of Classification Search
CPC ......... A61B 6/032; A61B 6/4035; A61B 6/42; A61B 6/4233; A61B 6/4241; A61B 6/482
USPC ..... 378/5, 19, 98.8, 98.9, 98.11; 250/370.09
See application file for complete search history.

(56) References Cited

U.S. PATENT DOCUMENTS

| | | | | |
|---|---|---|---|---|
| 6,563,906 B2 * | 5/2003 | Hussein | ............... | G01B 15/025 378/86 |
| 7,092,481 B2 * | 8/2006 | Hoffman | ............... | A61B 6/4241 250/370.09 |
| 7,127,027 B2 * | 10/2006 | Hoffman | ............... | A61B 6/4241 250/370.09 |
| 7,236,559 B2 * | 6/2007 | Jha | ......................... | A61B 6/032 378/5 |
| 7,260,174 B2 * | 8/2007 | Hoffman | ................ | A61B 6/032 250/363.09 |
| 7,298,812 B2 * | 11/2007 | Tkaczyk | ................ | A61B 6/032 378/4 |

(Continued)

OTHER PUBLICATIONS

Katsuyuki Taguchi et al., Enabling Photon Counting Clinical X-ray CT, 2009 IEEE Nuclear Science Symposium Conference Record, 3581-3585.*

*Primary Examiner* — Allen C. Ho
(74) *Attorney, Agent, or Firm* — Oblon, McClelland, Maier & Neustadt, L.L.P.

(57) ABSTRACT

According to one embodiment, the X-ray tube generates X-rays. The X-ray detector detects the X-rays transmitted through a subject. The data acquisition circuitry acquires count data concerning a count number of the detected X-rays for energy bands. The memory circuitry stores data of a response function that associates incident X-rays on the X-ray detector with a response characteristic of a system including the X-ray detector and the data acquisition circuitry. The processing circuitry calculates an X-ray absorption amount of each of a plurality of base substances based on the count data concerning the energy bands acquired by the data acquisition circuitry, an energy spectrum of the incident X-rays, and the response function.

19 Claims, 8 Drawing Sheets

(56) References Cited

U.S. PATENT DOCUMENTS

| | | | | |
|---|---|---|---|---|
| 7,403,589 B1* | 7/2008 | Short | A61B 6/032 | 250/370.11 |
| 7,479,639 B1* | 1/2009 | Shahar | G01T 1/17 | 250/370.06 |
| 7,486,764 B2* | 2/2009 | Tkaczyk | G01T 1/249 | 250/370.09 |
| 7,512,210 B2* | 3/2009 | Possin | A61B 6/032 | 250/370.09 |
| 7,532,703 B2* | 5/2009 | Du | A61B 6/032 | 378/116 |
| 7,573,040 B2* | 8/2009 | Tkaczyk | G01T 1/242 | 250/370.09 |
| 7,583,779 B2* | 9/2009 | Tkaczyk | A61B 6/032 | 378/4 |
| 7,583,790 B2* | 9/2009 | Hoffman | A61B 6/032 | 250/370.09 |
| 7,606,347 B2* | 10/2009 | Tkaczyk | A61B 6/032 | 378/19 |
| 7,613,274 B2* | 11/2009 | Tkaczyk | A61B 6/032 | 378/19 |
| 7,646,845 B2* | 1/2010 | Lecomte | A61B 6/032 | 378/19 |
| 7,696,483 B2* | 4/2010 | Tkaczyk | G01T 1/171 | 250/370.06 |
| 7,697,657 B2* | 4/2010 | Walter | A61B 6/4241 | 378/4 |
| 7,724,865 B2* | 5/2010 | Wu | A61B 6/032 | 378/4 |
| 7,738,625 B2* | 6/2010 | Nishide | A61B 6/032 | 378/19 |
| 7,756,239 B2* | 7/2010 | Wu | A61B 6/032 | 378/4 |
| 7,760,123 B2* | 7/2010 | Rao | G06G 7/18 | 341/155 |
| 7,822,169 B2* | 10/2010 | Roessl | G06T 5/50 | 378/4 |
| 7,829,860 B2* | 11/2010 | Nygard | G01T 1/2018 | 250/366 |
| 7,869,862 B2* | 1/2011 | Seppi | A61B 6/032 | 600/420 |
| 7,881,908 B2* | 2/2011 | Eversmann | G01T 1/247 | 702/189 |
| 7,885,372 B2* | 2/2011 | Edic | A61B 6/032 | 378/158 |
| 7,916,836 B2* | 3/2011 | Tkaczyk | G01T 1/24 | 250/370.09 |
| 7,924,969 B2* | 4/2011 | Yamakawa | A61B 6/032 | 378/5 |
| 8,111,803 B2* | 2/2012 | Edic | A61B 6/4035 | 378/146 |
| 8,194,820 B2* | 6/2012 | Wang | G01N 23/087 | 378/53 |
| 8,243,874 B2* | 8/2012 | Carmi | G01T 1/2985 | 250/366 |
| 8,315,352 B2* | 11/2012 | Wu | A61B 6/032 | 378/18 |
| 8,389,928 B2* | 3/2013 | Hackenschmied | G01T 1/249 | 250/252.1 |
| 8,457,274 B2* | 6/2013 | Arodzero | G01V 5/0041 | 378/53 |
| 8,619,943 B2* | 12/2013 | Flohr | A61B 6/032 | 378/19 |
| 8,653,471 B2* | 2/2014 | Proksa | A61B 6/032 | 250/363.01 |
| 8,855,395 B2* | 10/2014 | Baturin | A61B 6/032 | 378/62 |
| 8,913,711 B2* | 12/2014 | Moriyasu | A61B 6/03 | 378/4 |
| 8,929,508 B1* | 1/2015 | Alvarez | G01N 23/087 | 378/18 |
| 9,014,330 B2* | 4/2015 | Takayama | A61B 6/032 | 250/363.02 |
| 9,044,189 B2* | 6/2015 | Flohr | A61B 6/032 | |
| 9,052,266 B2* | 6/2015 | Miyazaki | A61B 6/4241 | |
| 9,135,728 B2* | 9/2015 | Fan | A61B 6/06 | |
| 9,208,585 B2* | 12/2015 | Leng | A61B 6/032 | |
| 9,213,108 B2* | 12/2015 | Nagai | A61B 6/4233 | |
| 9,269,168 B2* | 2/2016 | Inglese | A61B 6/4241 | |
| 9,310,496 B2* | 4/2016 | Kang | G01T 7/005 | |
| 9,316,745 B2* | 4/2016 | Noshi | G01T 1/17 | |
| 9,318,518 B2* | 4/2016 | Hermann | H01L 27/14609 | |
| 9,320,477 B2* | 4/2016 | Liu | A61B 6/032 | |
| 9,337,233 B1* | 5/2016 | Palit | H01L 27/14663 | |
| 9,354,331 B2* | 5/2016 | Sagoh | A61B 6/032 | |
| 9,448,326 B2* | 9/2016 | Radley | G01N 23/087 | |
| 9,456,790 B2* | 10/2016 | Taguchi | A61B 6/4241 | |
| 9,476,993 B2* | 10/2016 | Wang | G01T 1/17 | |
| 9,488,739 B2* | 11/2016 | Pelc | G01T 1/247 | |
| 9,488,741 B2* | 11/2016 | Takagi | G01N 23/046 | |
| 9,495,772 B2* | 11/2016 | Shen | G01T 1/2985 | |
| 9,595,101 B2* | 3/2017 | Kato | G06T 11/005 | |
| 9,600,866 B2* | 3/2017 | Brendel | G06T 5/002 | |
| 9,610,055 B2* | 4/2017 | Taguchi | A61B 6/5205 | |
| 9,633,814 B2* | 4/2017 | Oikawa | A61B 6/405 | |
| 9,649,081 B2* | 5/2017 | Kang | A61B 6/405 | |
| 9,655,583 B2* | 5/2017 | Proksa | A61B 6/54 | |
| 9,662,077 B2* | 5/2017 | Moriyasu | A61B 6/4241 | |
| 9,678,220 B2* | 6/2017 | Herrmann | G01T 1/17 | |
| 9,693,743 B2* | 7/2017 | Arakita | G01T 1/1606 | |
| 9,808,210 B2* | 11/2017 | Yamazaki | A61B 6/032 | |
| 9,808,216 B2* | 11/2017 | Schmidt | A61B 6/583 | |
| 9,829,586 B2* | 11/2017 | Göderer | G01T 1/24 | |
| 9,903,964 B2* | 2/2018 | Thran | G01T 1/244 | |
| 9,913,622 B2* | 3/2018 | Ida | A61B 6/5205 | |
| 9,949,710 B2* | 4/2018 | Kang | A61B 6/54 | |
| 9,977,140 B2* | 5/2018 | Wang | G01T 7/005 | |

\* cited by examiner

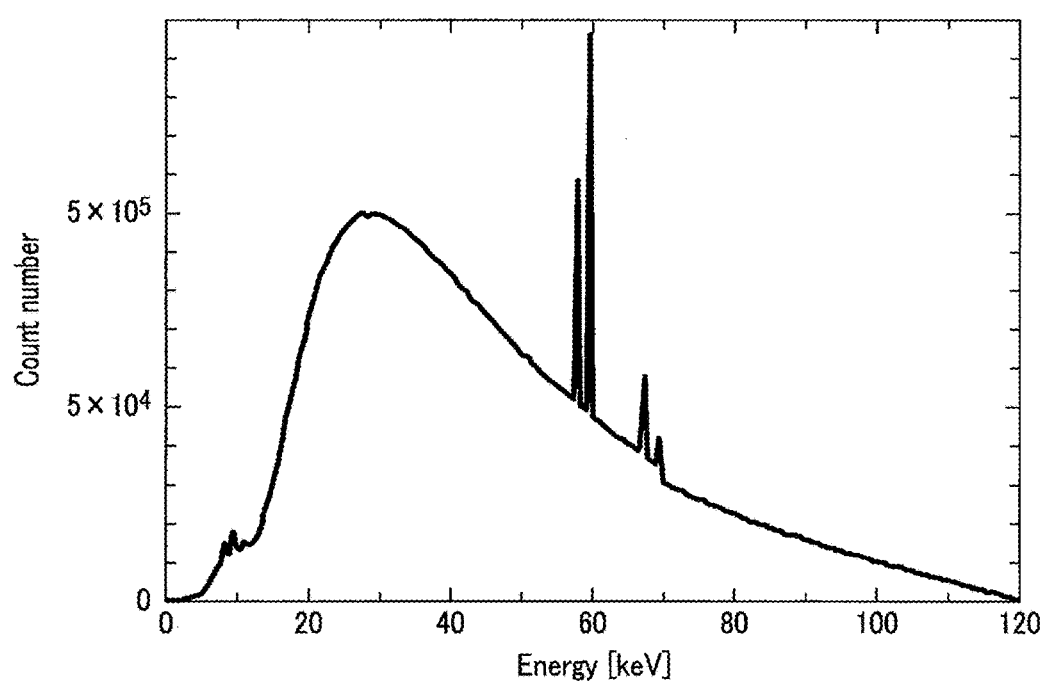
F I G. 2

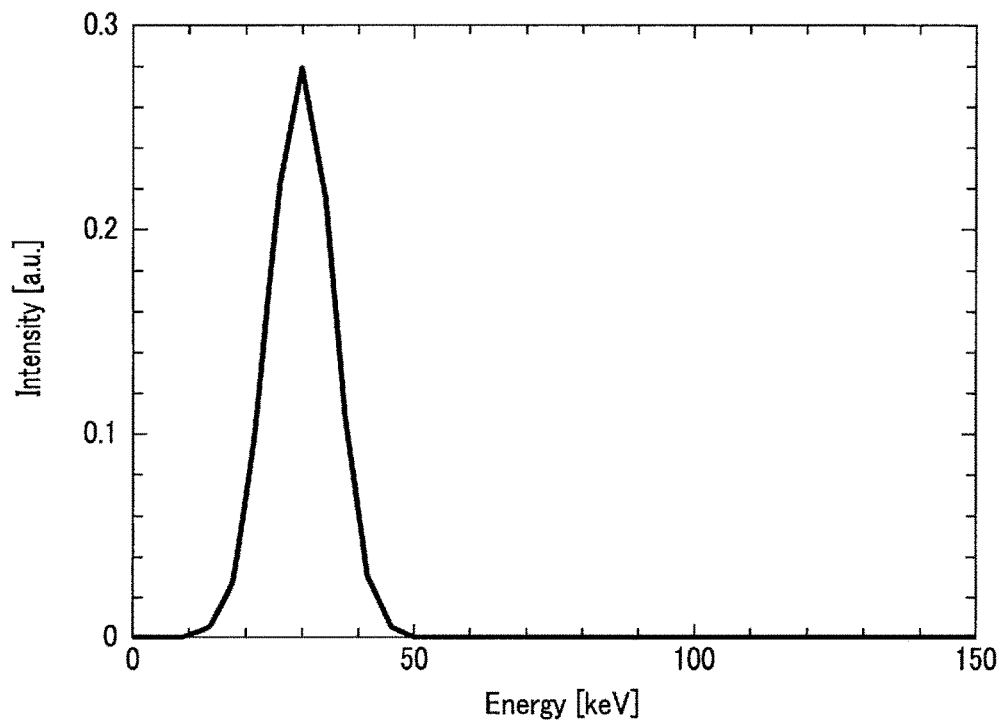
F I G. 3
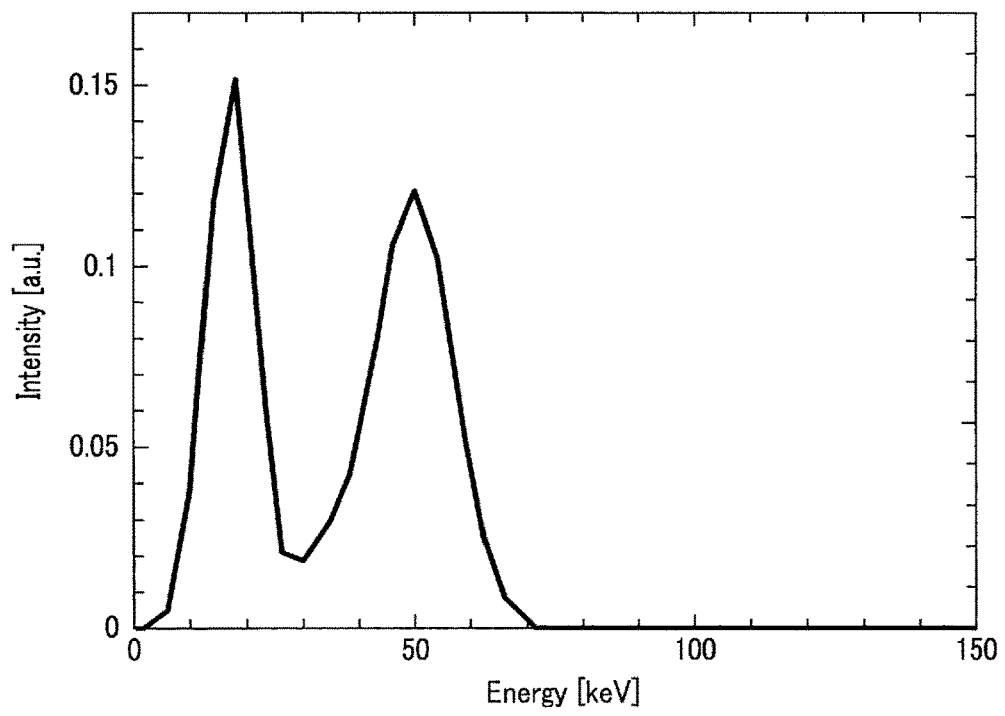
F I G. 4

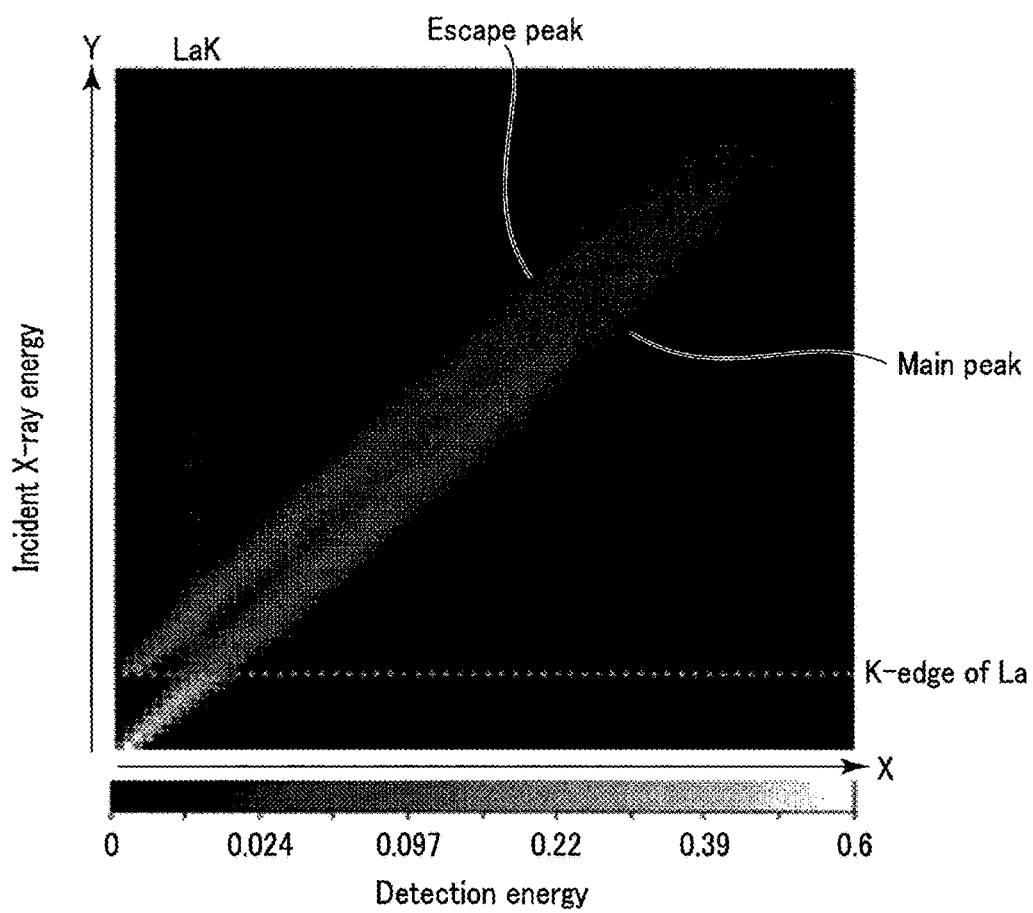
F I G. 5

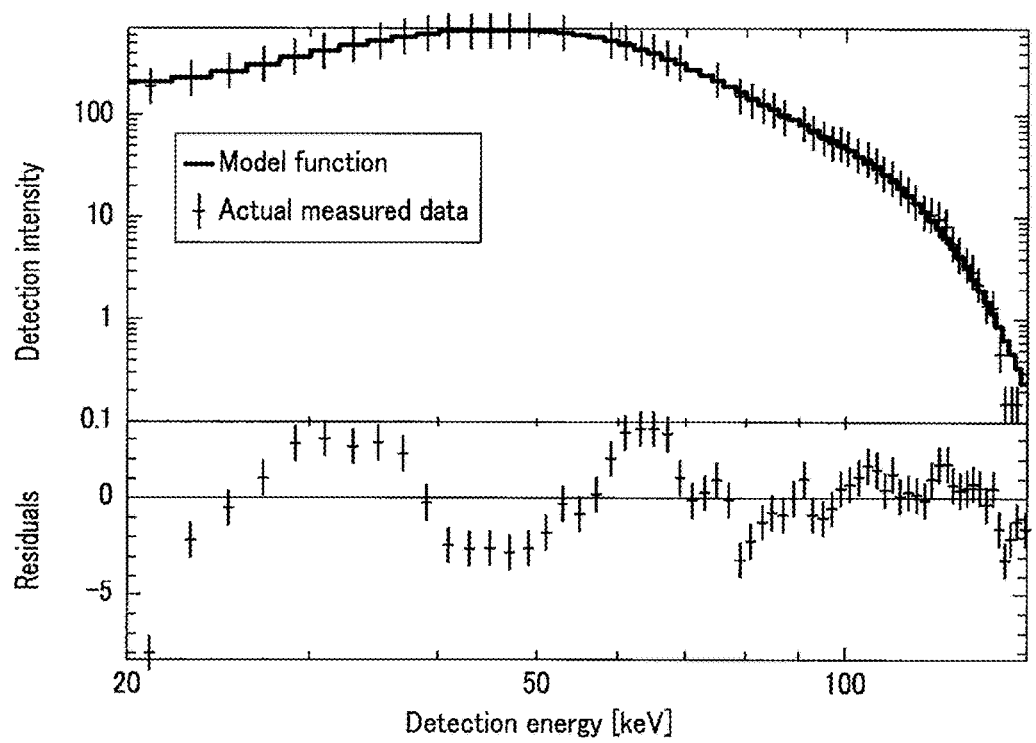
F I G. 6

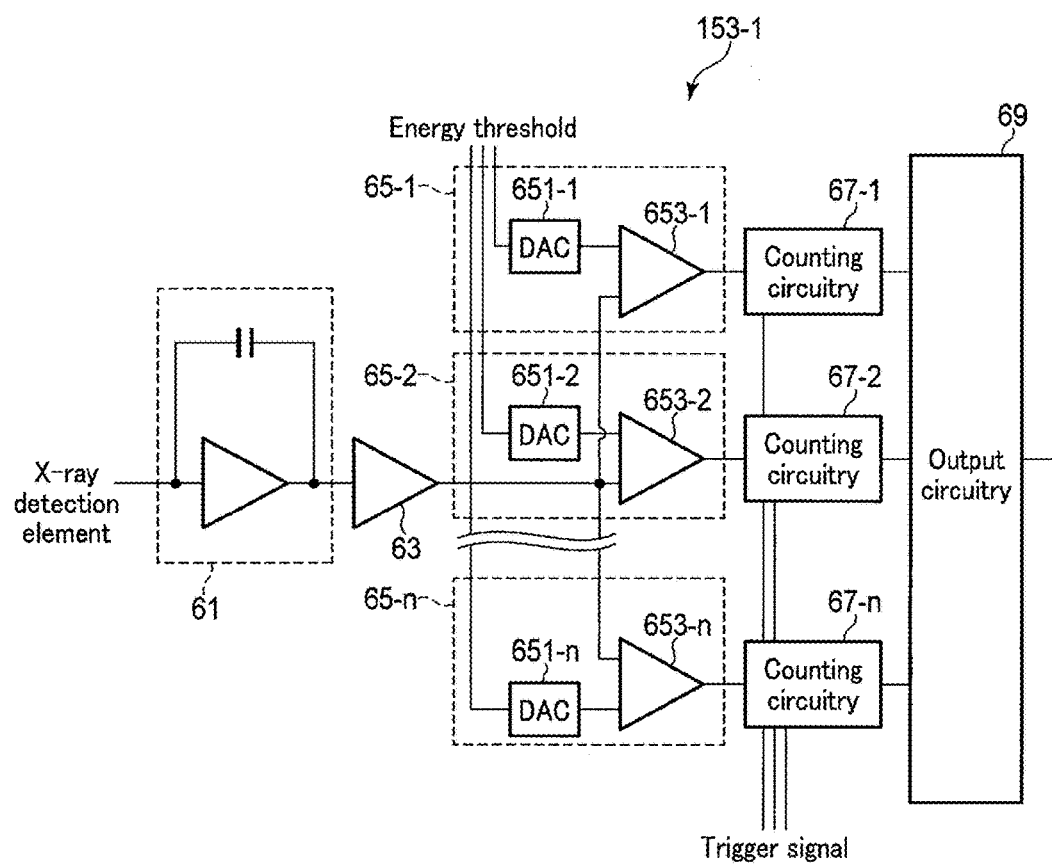
F I G. 7

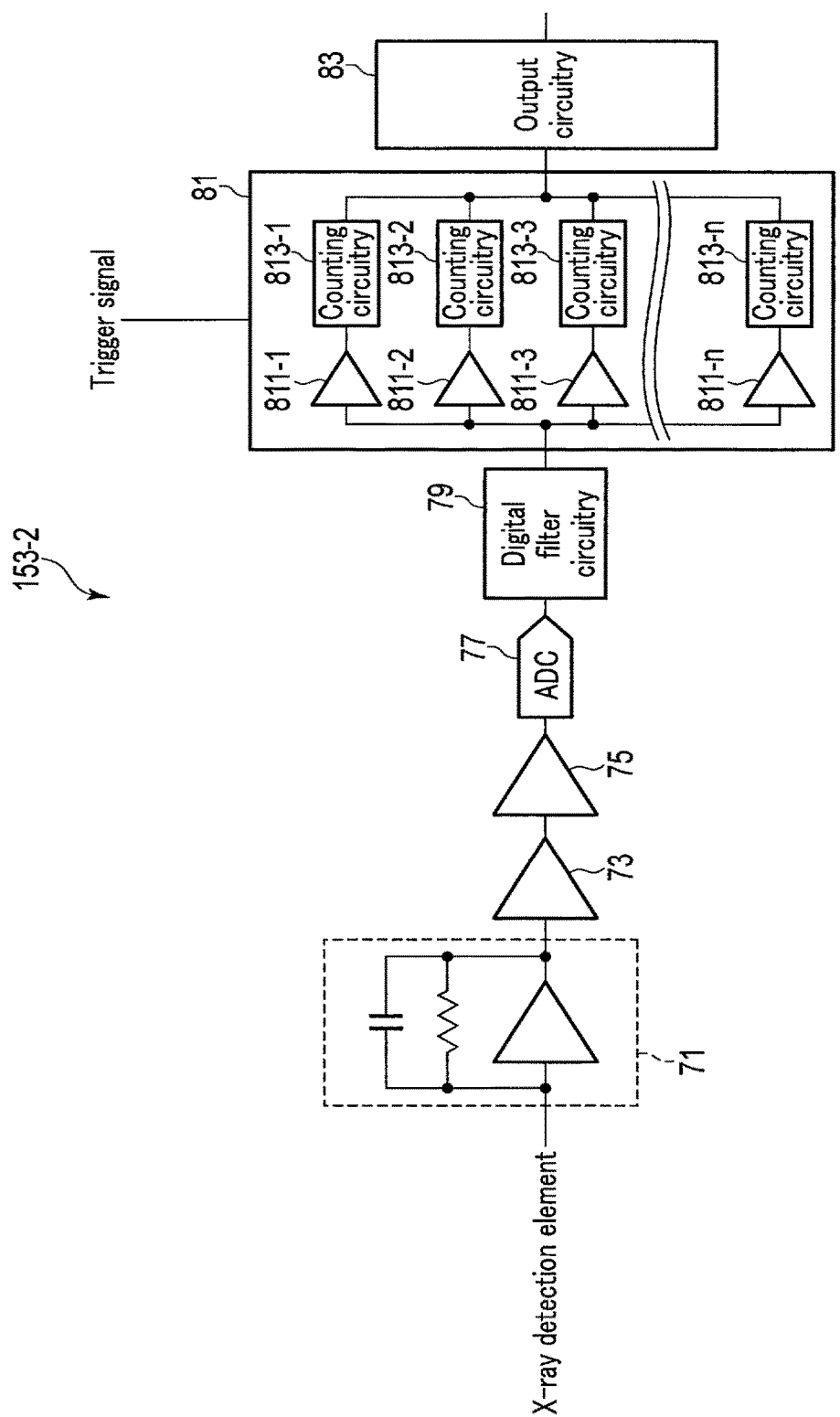
F I G. 8

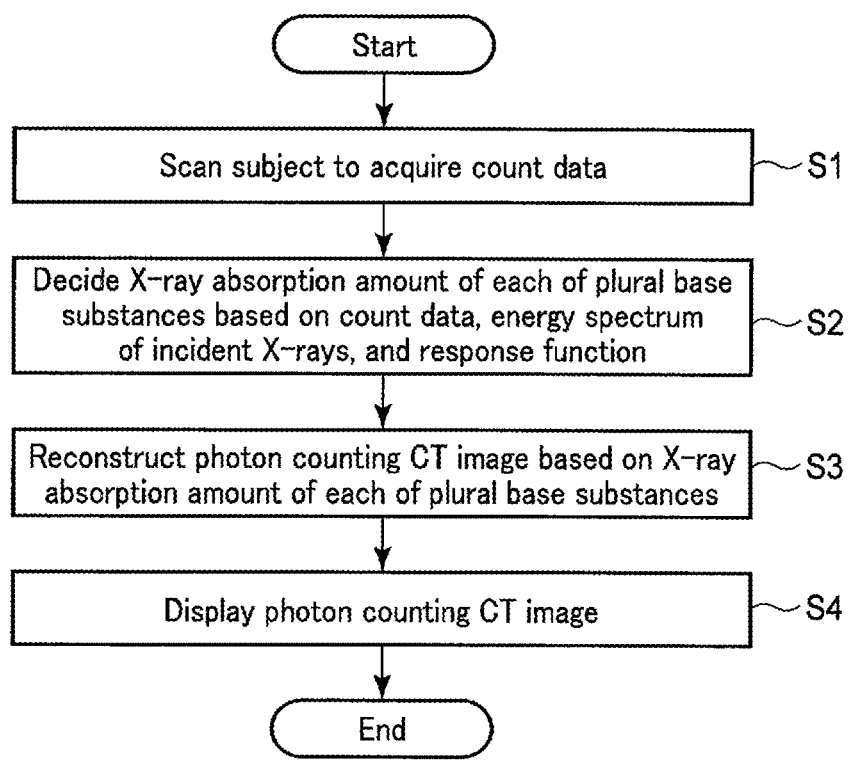
F I G. 9

PHOTON COUNTING APPARATUS

CROSS-REFERENCE TO RELATED APPLICATIONS

This application is based upon and claims the benefit of priority from the prior Japanese Patent Application No. 2014-203368, filed Oct. 1, 2014 and the prior Japanese Patent Application No. 2015-191306, filed Sep. 29, 2015, the entire contents of all of which are incorporated herein by reference.

FIELD

Embodiments described herein relate generally to a photon counting apparatus.

BACKGROUND

A photon counting apparatus such as a photon counting CT apparatus detects X-rays of a high dose on a photon basis and discriminates a substance that the X-rays have passed through. In the photon counting apparatus, a direct type detector such as a semiconductor detector having an excellent energy resolving power is used to discriminate a substance. As a readout circuitry used to read out a signal from the detector, a highly integrated element such as an ASIC is assumed to be used. Regardless of its high energy resolving power, the semiconductor detector has many problems such as a high cost and poor stability when used in the photon counting apparatus. On the other hand, an X-ray computed tomography apparatus uses an indirect type detector. The indirect type detector is formed by combining a phosphor such as a scintillator and a photodetector such as a photomultiplier. Such an indirect type detector is field-proven as a detector for an X-ray CT and features a low cost and high stability, as compared to the semiconductor detector. However, because of a low energy resolving power, it is very difficult to discriminate a substance.

BRIEF DESCRIPTION OF THE DRAWING

FIG. 2 is a graph showing an energy spectrum $I_0(E)$ of X-rays generated by an X-ray tube without a wedge filter;

FIG. 3 is a graph showing the output of a standard detection system using LaBr3 as a scintillator with respect to monochromatic X-rays;

FIG. 4 is a graph showing the output of the standard detection system using LaBr3 as a scintillator with respect to other monochromatic X-rays;

FIG. 5 is a graph schematically showing a response function according to the embodiment;

FIG. 6 is a graph showing comparison between an energy spectrum represented by count data of actual measurement and an energy spectrum represented by a model function;

FIG. 7 is a block diagram showing an example of the arrangement of a data acquisition circuitry according to the embodiment;

FIG. 8 is a block diagram showing another example of the arrangement of the data acquisition circuitry according to the embodiment; and FIG. 9 is a flowchart showing the typical procedure of photon counting CT imaging performed under the control of a system control circuitry shown in FIG. 1.

DETAILED DESCRIPTION

Figure 1:
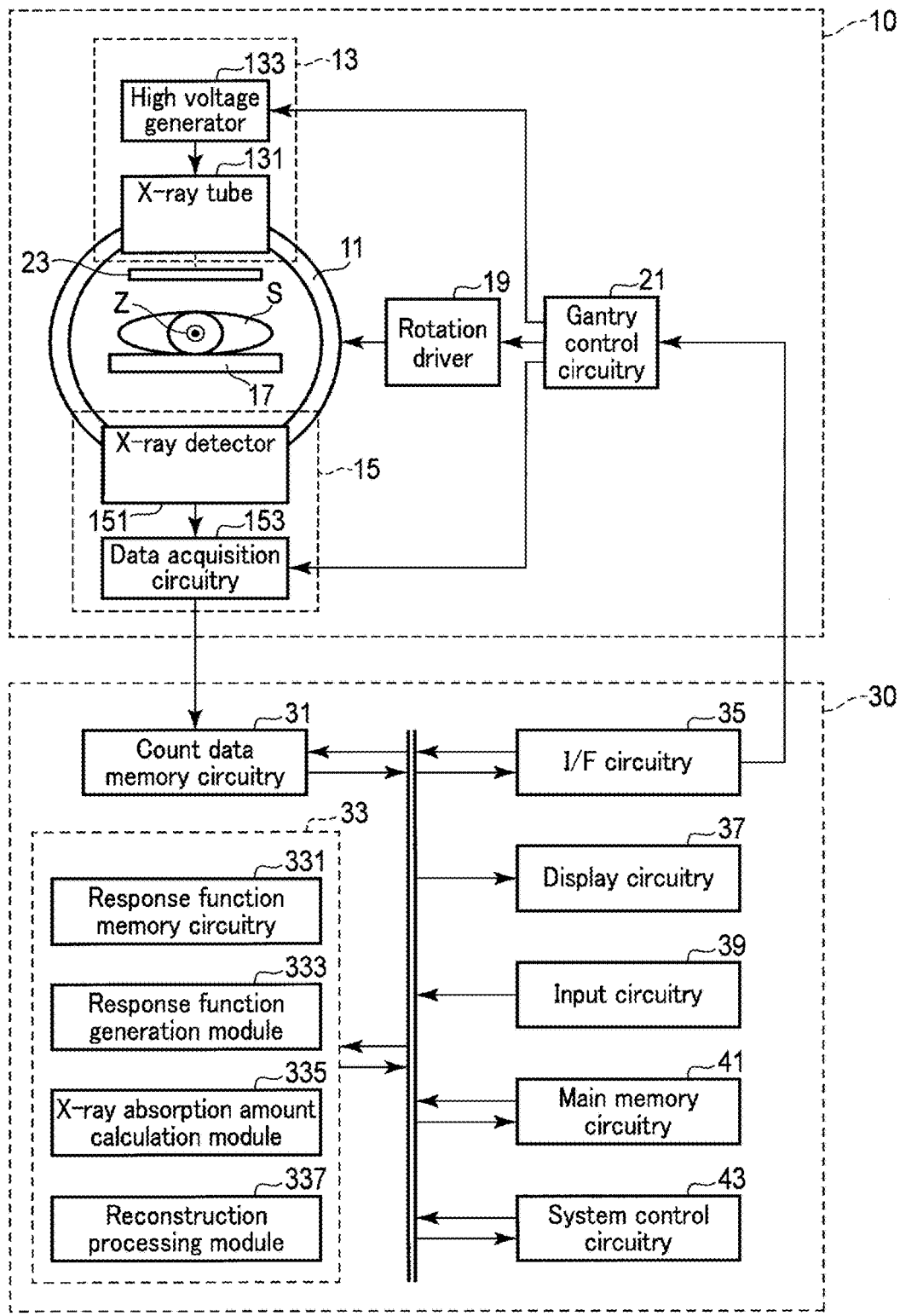
FIG. 1 is a block diagram showing the arrangement of a photon counting CT apparatus according to the embodiment.

In general, according to one embodiment, a photon counting apparatus includes an X-ray tube, an X-ray detector, a data acquisition circuitry, a memory circuitry, and a processing circuitry. The X-ray tube generates X-rays. The X-ray detector detects the X-rays generated by the X-ray tube and transmitted through a subject. The data acquisition circuitry acquires count data concerning a count number of the detected X-rays for a plurality of energy bands based on an output signal from the X-ray detector. The memory circuitry stores data of a response function that associates incident X-rays on the X-ray detector with a response characteristic of a system including the X-ray detector and the data acquisition circuitry. The processing circuitry calculates an X-ray absorption amount of each of a plurality of base substances based on the count data concerning the plurality of energy bands acquired by the data acquisition circuitry, an energy spectrum of the incident X-rays generated by the X-ray tube, and the response function read out from the memory circuitry.

A photon counting apparatus according to the embodiment will now be described with reference to the accompanying drawings.

The photon counting apparatus according to the embodiment is applicable to any one of an X-ray CT type apparatus (to be referred to as a photon counting CT apparatus hereinafter) and an X-ray photography type apparatus (to be referred to as a photon counting XR apparatus hereinafter). The photon counting apparatus according to the embodiment will be described below in detail using a photon counting CT apparatus as a detailed example.

Various types of photon counting CT apparatuses can be assumed, including a rotate/rotate-type apparatus in which an X-ray tube and an X-ray detector integrally rotate around a subject and a stationary/rotate-type apparatus in which a number of X-ray detection elements arranged in a ring are fixed, and only an X-ray tube rotates around a subject. This embodiment is applicable to any type. However, in the following explanation, the photon counting CT apparatus is assumed to be a rotate/rotate-type apparatus.

As the data acquisition method of the photon counting CT apparatus, a sinogram mode in which the count number of X-ray photons in each view is counted and a list mode in which the energy value for each X-ray photon is recorded time-serially are known. This embodiment is applicable to any type. A photon counting CT apparatus of the sinogram mode will be exemplified below.

FIG. 1 is a block diagram showing the arrangement of the photon counting CT apparatus according to the embodiment. As shown in FIG. 1, the photon counting CT apparatus according to this embodiment includes a gantry 10 and a console 30. The gantry 10 supports a rotating frame 11 having a cylindrical shape rotatably about a rotation axis Z. An X-ray generation system 13 and an X-ray detection system 15 are attached to the rotating frame 11 so as to face each other with respect to the rotation axis Z. An FOV (Field Of View) is set for the bore of the rotating frame 11. A top plate 17 is inserted into the bore of the rotating frame 11. A subject S is placed on the top plate 17. The top plate 17 is positioned such that the imaging portion of the subject S placed on the top plate 17 is included in the FOV. The rotating frame 11 receives power from a rotation driver 19 and rotates about the rotation axis Z at a predetermined angular velocity. The rotation driver 19 generates the power to rotate the rotating frame 11 in accordance with a control signal from a gantry control circuitry 21.

The X-ray generation system 13 generates X-rays in accordance with a control signal from the gantry control circuitry 21. More specifically, the X-ray generation system 13 includes an X-ray tube 131 and a high voltage generator 133. Upon receiving high voltage application and filament current supply from the high voltage generator 133, the X-ray tube 131 generates X-rays. The high voltage generator 133 applies a high voltage according to a control signal from the gantry control circuitry 21 to the X-ray tube 131, and supplies a filament current according to a control signal from the gantry control circuitry 21 to the X-ray tube 131.

The X-ray detection system 15 detects X-rays generated by the X-ray generation system 13 and transmitted through the subject S, and acquires, for a plurality of energy bands, count data that expresses the number of detected X-rays. More specifically, the X-ray detection system 15 includes an X-ray detector 151 and a data acquisition circuitry 153.

The X-ray detector 151 detects X-rays generated by the X-ray tube 131 and transmitted through the subject S. The X-ray detector 151 includes a plurality of X-ray detection elements that are two-dimensionally arranged. More specifically, the X-ray detector 151 is assumed to be an indirect type detector. In this case, each X-ray detection element includes a phosphor (scintillator) that converts X-rays into fluorescence, and a photodetector that converts the fluorescence into an electric signal. In this embodiment, the scintillator detects X-ray photons from the X-ray tube 131, and generates fluorescent photons in a number corresponding to the energy of the detected X-ray photons. The plurality of fluorescent photons are detected by the photodetector. The photodetector converts the plurality of detected fluorescent photons into a current signal by photoelectric conversion and amplifies the current signal. The current signal (electric signal) from the photodetector is supplied to the data acquisition circuitry 153. The electric signal has a peak value corresponding to the energy of the incident X-ray photons. The scintillator according to this embodiment can contain, as a material, any existing luminescent material, for example, LaBr3 which generates fluorescence in reaction to X-rays.

Note that as the X-ray detector 151 according to this embodiment, not an indirect type detector but a direct type detector may be used. As the direct type X-ray detector 151, for example, a type including a semiconductor diode formed by attaching electrodes to the two ends of a semiconductor is applicable. X-ray photons that have entered the semiconductor are converted into electron-hole pairs. The number of electron-hole pairs generated by entering of one X-ray photon depends on the energy of the incident X-ray photon. The electrons and holes are attracted by the pair of electrodes formed at the two ends of the semiconductor. The pair of electrodes generates electrical pulses having a peak value corresponding to the charge of an electron-hole pair. One electrical pulse has a peak value corresponding to the energy of the incident X-ray photon.

The data acquisition circuitry 153 acquires count data that expresses the count number of X-rays detected by the X-ray detector 151 for a plurality of energy bands in accordance with a control signal from the gantry control circuitry 21. The count data concerning the plurality of energy bands corresponds to an energy spectrum concerning the incident X-rays on the X-ray detector 151, which is deformed in accordance with the response characteristic of the X-ray detection system 15. The response characteristic of a system (standard detection system) including an X-ray detector and a data acquisition circuitry will be referred to as a detector response characteristic hereinafter.

A wedge filter 23 is attached to the X ray tube 131. The wedge filter 23 is an X ray filter used to almost uniform the spatial dose distribution of X rays that enter the X ray detector 151. The wedge filter 23 is formed by a substance having a relatively small atomic number, for example, aluminum. Typically, the wedge filter 23 is formed so as to be thick from the center to the ends in the channel direction of the X ray detector 151. Note that the wedge filter 23 may be omitted if unnecessary.

The gantry control circuitry 21 generally controls various devices on the gantry 10. For example, the gantry control circuitry 21 controls the X-ray generation system 13, the X-ray detection system 15, and the rotation driver 19 to execute photon counting CT imaging of the subject S. The rotation driver 19 rotates at a predetermined angular velocity under the control of the gantry control circuitry 21. The high voltage generator 133 of the X-ray generation system 13 applies a high voltage corresponding to a set tube voltage value to the X-ray tube 131 and supplies a filament current to the X-ray tube 131 under the control of the gantry control circuitry 21. The data acquisition circuitry 153 of the X-ray detection system 15 acquires count data on a view basis for each of a plurality of energy bands in synchronism with view switching under the control of the gantry control circuitry 21.

As hardware resources, the gantry control circuitry 21 includes a processor such as a CPU (Central Processing Unit) or MPU (Micro Processing Unit), and memories such as a ROM (Read Only Memory) and RAM (Random Access Memory). The gantry control circuitry 21 may be provided on the gantry 10, the console 30, or a device separated from the gantry 10 and the console 30. The gantry control circuitry 21 may be implemented by an application specific integrated circuitry (ASIC), a field programmable logic device (FPGA), another complex programmable logic device (CPLD), or a simple programmable logic device (SPLD). The processor implements the above-described function by reading out a program saved in the memories and executing it. Note that instead of saving the program in the memories, the program may directly be incorporated in a circuitry of the processor. In this case, the processor implements the above-described function by reading out the program incorporated in the circuitry and executing it.

The console 30 includes a count data memory circuitry 31, a reconstruction circuitry 33, an I/F circuitry 35, a display circuitry 37, an input circuitry 39, a main memory circuitry 41, and a system control circuitry 43. The count data memory circuitry 31, the reconstruction circuitry 33, the I/F circuitry 35, the display circuitry 37, the input circuitry 39, the main memory circuitry 41, and the system control circuitry 43 are connected via a bus.

The count data memory circuitry 31 is memories such as an HDD (Hard Disk Drive), an SSD (Solid State Drive), or an integrated circuitry memory device. More specifically, the count data memory circuitry 31 stores count data concerning a plurality of energy bands, which is transmitted from the gantry 10. The count data memory circuitry 31 may also store data of an X-ray absorption amount calculated by an X-ray absorption amount calculation module 335. The X-ray absorption amount will be described later.

The reconstruction circuitry 33 reconstructs a photon counting CT image concerning the subject S based on the count data. More specifically, the reconstruction circuitry 33 includes a response function memory circuitry 331. The response function memory circuitry 331 stores data of a response function that associates incident X-rays on the X-ray detector 151 with the detector response characteristic.

The response function defines the relationship between detection energy for each incident X-ray and the output response of the system. For example, the response function defines the relationship between detection intensity and detection energy for each incident X-ray. The detection energy corresponds to the energy of X-ray photons measured by the standard detection system in response to detection of X-ray photons having the incident X-ray energy. More specifically, the detection energy is a value obtained by multiplying the peak value of an analog electric signal input to a discrimination circuitry (to be described later) or the data value of a digital signal by a predetermined conversion factor. The detection intensity corresponds to the intensity of X-rays having the incident X-ray energy, in other words, the count number of X-ray photons. The response function is generated in advance by a response function generation module 333 or another processor. Details of the response function will be described later.

The standard detection system indicates a system formed from an X-ray detector and a data acquisition circuitry used to acquire an actual measured value for response function generation. To attain a high substance discrimination capability, the standard detection system and the X-ray detection system 15 according to this embodiment preferably have the same structure. For example, all factors that affect the detector response characteristic, such as the scintillator material, circuitry arrangement, and sampling speed are preferably identical in the standard detection system and the X-ray detection system 15 according to this embodiment. Note that some of these factors may be different if the influence on the detector response characteristic is small. The X-ray detection system 15 included in the photon counting CT apparatus according to this embodiment may be used to acquire an actual measured value for response function generation. In this case, the standard detection system indicates the X-ray detection system 15.

As shown in FIG. 1, the reconstruction circuitry 33 may include, as hardware resources, a processor such as a CPU, MPU, or GPU (Graphics Processing Unit), and memories such as a ROM and RAM, in addition to the response function memory circuitry 331. The processor implements a response function generation module 333, an X ray absorption amount calculation module 335, and a reconstruction processing module 337 by reading out a reconstruction program saved in the memories and executing it.

By executing the response function generation module 333, the reconstruction circuitry 33 generates data of a response function that expresses the detector response characteristic. For example, the reconstruction circuitry 33 measures the response (that is, detection energy and detection intensity) of the standard detection system to a plurality of monochromatic X-rays having a plurality of incident X-ray energies by predictive calculations, experiments, and a combination of predictive calculations and experiments, and generates a response function based on the measured values of detection energy and detection intensity. The reconstruction circuitry 33 may generate data of a response function based on actual measured values acquired in calibration or the like. The generated data of the response function is stored in the response function memory circuitry 331. Note that the data of the response function to be stored in the response function memory circuitry 331 need not always be generated by the reconstruction circuitry 33. The data of the response function may be generated by a computer apparatus in another facility. In this case, the data may be transmitted from the computer apparatus to the photon counting CT apparatus according to this embodiment, or read out from a portable memory medium that stores the data of the response function to the photon counting CT apparatus according to this embodiment.

By executing the X-ray absorption amount calculation module 335, the reconstruction circuitry 33 calculates an X-ray absorption amount concerning each of a plurality of base substances based on count data concerning the plurality of energy bands, the energy spectrum of the incident X-rays on the subject S, and the response function stored in the response function memory circuitry 331. The reconstruction circuitry 33 calculates the X-ray absorption amount based on the count data and the energy spectrum of the incident X-rays on the subject S using the response function, thereby calculating an X-ray absorption amount without the influence of the response characteristic of the X-ray detection system 15. Processing of obtaining the X-ray absorption amount for each base substance is also called substance discrimination. All substances such as calcium, calcification, bone, fat, muscle, air, organ, lesion, hard tissue, soft tissue, and contrast substance can be set as the base substance. The type of the calculation target base substance is decided in advance by a user or the like via the input circuitry 39 and the like. The X-ray absorption amount represents the amount of X-rays absorbed by the base substance. More specifically, the X-ray absorption amount is defined by a combination of an X-ray attenuation coefficient and an X-ray transmission path length.

By executing the reconstruction processing module 337, the reconstruction circuitry 33 reconstructs a photon counting CT image that expresses the spatial distribution of an imaging target base substance out of a plurality of base substances, based on the X-ray absorption amount concerning each of the plurality of base substances calculated by the X-ray absorption amount calculation module 335. The imaging target base substance can include one type of base substance or a plurality of types of base substances. The imaging target base substance can be set via the input circuitry 39 or automatically arbitrarily.

Note that the response function generation module 333, the X ray absorption amountcalculation module 335, and the reconstruction processing module 337 are assumed to be implemented by executing the reconstruction program by the processor. However, the embodiment is not limited to this. For example, the reconstruction circuitry 33 may include a processing circuitry for the response function generation module 333, a processing circuitry for the X ray absorption amount calculation module 335, and a processing circuitry for the reconstruction processing module 337. Each of these processing circuitry may be implemented by ASIC, FPGA, CPLD, or SPLD.

The I/F circuitry 35 is an interface for communication between the console 30 and the gantry 10. For example, the I/F circuitry 35 supplies an imaging start signal, imaging stop signal, and the like from the system control circuitry 43.

The display circuitry 37 displays a photon counting CT image or the like on a display device. As the display device, for example, a CRT display, a liquid crystal display, an organic EL display, or a plasma display can appropriately be used.

The input circuitry 39 receives various kinds of instructions and information input from the user via an input device. As the input device, a keyboard, a mouse, various kinds of switches, and the like are usable.

The main memory circuitry 41 is a memory device that stores various kinds of information. For example, the main main memory circuitry 41 stores the image generation program of a photon counting CT image according to this embodiment, and the like.

The system control circuitry 43 functions as the center of the photon counting CT apparatus according to this embodiment. The system control circuitry 43 reads out an imaging program according to this embodiment from the main memory circuitry 41, and controls various kinds of constituent elements in accordance with the imaging program. Photon counting CT imaging for generating a photon counting CT image according to this embodiment is thus performed.

The response function according to this embodiment will be described next.

Generally, in dual energy CT, substance discrimination is performed in accordance with below equation (1).

$$I_{det}(E) = I_0(E)\exp(-\mu_0(E)L_0 - \mu_1(E)L_1) \quad (1)$$

In the equation (1), E is the energy of X-rays, and $I_{det}(E)$ is the energy spectrum of X-rays measured by the standard detection system. Note that the energy spectrum indicates the energy distribution of X-ray intensities. $I_0(E)$ is the energy spectrum of X-rays that enter the subject S. When the wedge filter is used, $I_0(E)$ represents the energy spectrum of X-rays that enter the object after passing through the wedge filter. When the wedge filter is not used, $I_0(E)$ represents the energy spectrum of X-rays emitted by the X-ray tube. In addition, $\mu_0(E)$ is the X-ray attenuation coefficient of a base substance 0, and $L_0$ is the path length (transmission path length) of X-rays transmitted through the base substance 0. Similarly, $\mu_1(E)$ is the X-ray attenuation coefficient of a base substance 1, and $L_1$ is the path length (transmission path length) of X-rays transmitted through the base substance 1. $\mu_0(E)L_0$ is the X-ray absorption amount concerning the base substance 0, and $\mu_1(E)L_1$ is the X-ray absorption amount concerning the base substance 1. Equation (1) includes two unknowns $\mu_0(E)L_0$ and $\mu_1(E)L_1$ which can be solved using two equations in theory. In current CT, different two data sets concerning two different tube voltages are acquired, thereby obtaining the solution to equation (1). Note that the data set indicates a set of data representing $I_{det}(E)$ and $I_0(E)$.

In photon counting CT as well, substance discrimination can be performed based on the same concept as the dual energy CT. In photon counting CT, one set of count data is used because data acquisition is performed using one tube voltage. However, when the energy band is divided into two parts, substance discrimination can be done based on two count data sets concerning the two energy bands. Independence of the two count data sets is a precondition for the concept. A direct type detector having an excellent energy resolving power can meet this precondition. However, an indirect type detector having a low energy resolving power cannot meet the precondition in many cases because of low independence.

Equation (1) actually holds for an ideal X-ray detection system. In actuality, substance discrimination can be described as below equation (2).

$$I_{det}(E) = \{I_0(E)\exp(-\mu_0(E)L_0 - \mu_1(E)L_1)\} \otimes R(E) \quad (2)$$

In the equation (2), $\otimes$ is a convolution operator. The right-hand side is called a model function. The model function describes the detector response characteristic of the X-ray detection system 15. $R(E)$ is a response function representing the detector response characteristic. The expression in braces represents the energy spectrum of X-rays immediately before entering the X-ray detection system 15. Equation (2) convolutes the energy spectrum of X-rays immediately before entering the X-ray detection system 15 by the response function of the X-ray detection system 15, thereby obtaining the energy spectrum of the X-rays measured by the X-ray detection system 15.

Here, the response function describes the detector response characteristic of the standard detection system to monochromatic X-rays. An ideal X-ray detector generates an output signal like a delta function having only a detection energy corresponding to incident X-ray energy. However, the output signal of an actual X-ray detector is distributed not as a delta function but as a Gaussian function because of the energy resolving power. In addition, the output signal often exhibits a complex structure such as a deviation from the Gaussian function or a continuous component caused by components on the low energy side (G. F. Knoll, "Radiation Detection and Measurement, Third Edition", Nikkan Kogyo Shimbun, 2001). Under a high dose, the response function further deforms due to pile-up, polarization, or the like.

As described above, since the indirect type detector has a low energy resolving power, the low independence between adjacent energy bands in equation (1) poses a problem. However, when the response function is correctly considered like equation (2), $\mu_0(E)L_0$ and $\mu_1(E)L_1$ can accurately be estimated.

A problem here is the number of energy bands. According to the concept of equation (1), energy bands as many as the unknowns suffice, and at least two energy bands suffice. In equation (2), however, many energy bands are needed to consider the response function.

FIG. 2 is a graph showing the energy spectrum $I_0(E)$ of X-rays generated by the X-ray tube without the wedge filter. In the graph of FIG. 2, the ordinate is defined as the count number, and the abscissa is defined as the energy [keV]. The anode target substance is tungsten, and the tube voltage is 120 kV. As shown in FIG. 2, the energy spectrum of the X-rays generated by the X-ray tube includes characteristic X-rays resulting from the anode target substance as well as continuous X-ray components from 0 keV to 120 keV corresponding to the tube voltage.

In actual photon counting CT imaging, the subject S exists between the X-ray tube and the X-ray detector. For this reason, the X-rays having the energy spectrum shown in FIG. 2 are attenuated by absorption to the subject S and then detected by the X-ray detection system 15. The energy spectrum of the detected X-rays is convoluted by the response function corresponding to the detector response characteristic.

FIG. 3 shows the output of the standard detection system using LaBr3 as a scintillator with respect to monochromatic X-rays. In FIG. 3, the ordinate is defined as the intensity [A.U.], and the abscissa is defined as the energy [keV]. Out of LaBr3, lanthanum La mainly reacts to X-rays. The k-edge of lanthanum is 38.9 keV. FIG. 3 shows the output of the standard detection system with respect to monochromatic X-rays of 30 keV. In this case, since the energy (30 keV) of the monochromatic X-rays that have entered the standard detection system is lower than the energy (38.9 keV) of the k-edge of lanthanum, the output of the standard detection system is distributed with a peak at the energy corresponding to 30 keV. The peak corresponding to the energy of the incident monochromatic X-rays is called a main peak. The energy width of the main peak represents the energy resolving power of the standard detection system concerning the energy of the main peak.

FIG. 4 shows the output of the standard detection system using LaBr3 as a scintillator with respect to other monochromatic X-rays. FIG. 4 shows the output of the standard detection system with respect to monochromatic X-rays of 50 keV. In this case, since the energy (50 keV) of the monochromatic X-rays that have entered the standard detection system is higher than the energy (38.9 keV) of the k-edge of lanthanum, the output of the standard detection system is distributed not only with the main peak at the energy corresponding to 50 keV but also with a peak near 17 keV. This peak is called an escape peak. When the energy of monochromatic X-rays that have entered the standard detection system is higher than the energy of the k-edge of lanthanum, the lanthanum which absorbs (photoelectrically absorbs) the X-rays and jumps an excited state often emits the k-characteristic X-rays of lanthanum when the lanthanum falls from the excited state to the ground state. If the k-characteristic X-rays escape without being absorbed by the scintillator, the scintillator absorbs an energy (about 17 keV) obtained by subtracting the energy (about 33 keV) of the k-characteristic X-rays from the incident X-ray energy. The escape peak is a peak corresponding to the energy (about 17 keV) equivalent to the difference between the incident X-ray energy and the energy (about 33 keV) of the k-characteristic X-rays.

FIG. 5 is a graph schematically showing the response function according to this embodiment. The response function according to this embodiment is defined by, for example, a function including the incident X-ray energy [keV], the detection energy [keV], and the detection intensity [A.U.] as variables. In the graph of FIG. 5, the detection intensity is assigned to an orthogonal coordinate system in which the ordinate (y-axis) is defined as the incident X-ray energy, and the abscissa (x-axis) is defined as the energy [keV]. In FIG. 5, the detection intensity is expressed by shading.

In other words, the response function according to this embodiment defines the relationship between the detection energy and the detection intensity for each of a plurality of incident X-ray energies. For example, a response function representing the detector response characteristic for a certain incident X-ray energy is expressed as a cross section of the graph of FIG. 5 at the incident X-ray energy. As shown in FIG. 5, the main peak is observed at a point corresponding to Y=X. The dotted line corresponds to the energy of the k-edge of lanthanum. In the incident X-ray energies higher than the energy of the k-edge of lanthanum, escape peaks are observed at a predetermined interval on the low detection energy side of the main peak. The detection energy difference between the main peak and the escape peak corresponds to the detection energy equivalent to the energy of the k-characteristic X-rays of lanthanum. In addition, the peak of k-characteristic X-rays when the k-characteristic X-rays of lanthanum generated by another scintillator are absorbed by the scintillator is observed. Since the energy of the k-characteristic X-rays is constant, almost the same detection energy, that is, a detection energy parallel to the y-axis is observed independently of the incident X-ray energy. As described above, the response function according to this embodiment expresses a main peak corresponding to the incident X-ray energy, an escape peak corresponding to the incident X-ray energy to the energy of the k-characteristic X-rays of the scintillator material, and a peak corresponding to the energy of the k-characteristic X-rays of the scintillator material.

In the response function generation module 333 according to this embodiment, the reconstruction circuitry 33 measures the response of the standard detection system to a plurality of monochromatic X-rays having a plurality of incident X-ray energies by predictive calculations, experiments, and a combination of predictive calculations and experiments, and generates a response function based on the measured data. More specifically, the X-ray source irradiates the X-ray detector with monochromatic X-rays, and the X-ray detector detects the monochromatic X-rays. The detection energy and detection intensity of the X-ray detector are measured by an existing measurement device. The monochromatic X-rays are emitted sequentially from the lower limit energy to the upper limit energy of the energy range necessary for the response function. In the response function generation module 333, the reconstruction circuitry 33 records the measured detection energy and detection intensity for each incident X-ray energy of the emitted monochromatic X-rays. Note that if the wedge filter is used in the photon counting CT imaging, the standard detection system preferably detects the monochromatic X-rays transmitted through the wedge filter. In this case, in the response function generation module 333, the reconstruction circuitry 33 records the detection energy and detection intensity of the X-ray detector for the monochromatic X-rays transmitted through the wedge filter for each incident X-ray. The record of the detection energy and detection intensity for each incident X-ray is generated as the response function. Note that as for the response function, a mathematical model of a response function may be formed by predictive calculation, and the mathematical model may be corrected based on experimental values in a facility where high-intensity monochromatic X-rays such as synchrotron radiation can be obtained.

The energy spectrum of X-rays output from the X-ray detector has a shape obtained by attenuating the energy spectrum shown in FIG. 2 by object absorption in accordance with equation (2) and convoluting the energy spectrum of the X-rays that have undergone the object absorption by the response function shown in FIG. 4. The energy spectrum of the X-rays that have undergone the object absorption is expressed by the model function of equation (2).

FIG. 6 is a graph showing comparison between an energy spectrum represented by count data of actual measurement and an energy spectrum represented by the model function. The ordinate of the upper section of FIG. 6 is defined as the detection intensity (count number), and the abscissa represents the energy. The ordinate and abscissa are expressed as logarithms. Referring to FIG. 6, the range from 0 keV to 200 keV is divided into 128 energy bands. The widths of the energy bands are set identically. In the graph of the upper section, each count data of actual measurement is indicated by a cross, and the model function is indicted by a solid line. The lower section is a graph representing the difference (residual) between the energy spectrum represented by the count data of actual measurement and the energy spectrum represented by the model function. Data acquisition was conducted using a tube voltage of 120 kV and without a wedge filter and a subject (air). As can be seen from FIG. 6, the model function can generally reproduce the count data of actual measurement. In actuality, since a subject exists, an absorption structure further appears. The subject absorption can also be incorporated as a model function by assuming several base substances in accordance with equation (2).

However, as is apparent from FIG. 6, in a case where a base substance is quantitatively evaluated by convoluting a response function, if data sets, that is, energy bands as many as the unknowns are simply provided, a plurality of sets of solutions that meet equation (2) are obtained, and the substance and the absorption amount cannot be identified.

To obtain a solution in accordance with equation (2), at least 16, if possible, 50 or more energy bands preferably exist, as shown in FIG. 6.

This analysis scheme can cope with the below equation (3) in which the number of base substances is extended to three from equation (2).

$$I_{det}(E) = \{I_0(E)\exp(-\mu_0(E)L_0 - \mu_1(E)L_1 - \mu_2(E)L_2)\} \otimes R(E) \quad (3)$$

In the conventional dual energy CT, the k-edge of a base substance cannot be taken into consideration. However, in the image reconstruction method according to this embodiment, a k-edge structure can easily be reproduced by including the k-edge in the model function. Hence, by actively using a substance having a k-edge within the detection energy range, the image reconstruction method according to this embodiment can be applied to a k-edge imaging method as well, which enables high-contrast imaging that cannot be implemented by the dual energy CT.

The structure of the data acquisition circuitry 153 capable of setting many energy bands will be described below.

FIG. 7 is a block diagram showing an example of the arrangement of a data acquisition circuitry 153-1 according to this embodiment. Note that the data acquisition circuitry 153-1 includes readout channels as many as channels corresponding to the X-ray detection elements. The plurality of readout channels are parallelly implemented on an integrated circuitry such as an ASIC. FIG. 7 illustrates only the arrangement of the data acquisition circuitry 153-1 corresponding to one readout channel to avoid redundancy.

The data acquisition circuitry 153-1 shown in FIG. 7 includes a preamplifier circuitry 61, waveform shaping circuitry 63, a plurality of pulse height discrimination circuitry 65-1, 65-2, ..., 65-n, a plurality of counting circuitry 67-1, 67-2, ... 67-n, and output circuitry 69.

The preamplifier circuitry 61 amplifies a current signal from the X-ray detection element of a connection destination. More specifically, the preamplifier circuitry 61 converts a current signal from the X-ray detection element of the connection destination into a voltage signal having a voltage value (peak value) proportional to the charge amount of the current signal. The waveform shaping circuitry 63 is connected to the preamplifier circuitry 61. The waveform shaping circuitry 63 shapes the waveform of the voltage signal from the preamplifier circuitry 61. More specifically, the waveform shaping circuitry 63 reduces the pulse width of the voltage signal from the preamplifier circuitry 61.

A plurality of counting channels corresponding to the number of energy bands are connected to the waveform shaping circuitry 63. When n energy bands are set, n counting channels are provided. More specifically, n is preferably 16 or more, as described above. Each counting channel includes a pulse-height discrimination circuitry 65-n and a counting circuitry 67-n.

Each pulse-height discrimination circuitry 65-n discriminates the peak value of the voltage signal from the waveform shaping circuitry 63, that is, the energy of X-ray photons detected by the X-ray detection element. More specifically, the pulse-height discrimination circuitry 65-n includes a D/A conversion circuitry (DAC) 651-1. 651-2, ..., 651-n and a comparison circuitry 653-1. 653-2, ..., 653-n. The DAC 651-n inputs a digital signal (to be referred to as a digital threshold signal hereinafter) having a data value corresponding to an energy threshold from the gantry control circuitry 21 (not shown). The DAC 651-n converts the input digital threshold signal into an analog electric signal (to be referred to as an analog threshold signal hereinafter) having a peak value corresponding to the data value (energy threshold) of the digital threshold signal. Digital threshold signals corresponding to different thresholds are supplied from, for example, the gantry control circuitry 21 to the DACs 651-n. If the voltage signal from the waveform shaping circuitry 63 has a peak value corresponding to an energy band corresponding to the peak value (energy threshold) of the analog threshold signal from the DAC 651-n, the comparison circuitry 653-n outputs an electrical pulse signal. For example, if the peak value of the electrical pulse from the waveform shaping circuitry 63 is the peak value corresponding to an energy band bin 1, a comparison circuitry 653-1 for the energy band bin 1 outputs an electrical pulse signal. On the other hand, if the peak value of the electrical pulse from the waveform shaping circuitry 63 is not the peak value corresponding to the energy band bin 1, the comparison circuitry 653-1 for the energy band bin 1 does not output an electrical pulse signal.

The counting circuitry 67-n counts the electrical pulse signal from the pulse-height discrimination circuitry 65-n at a readout period that matches the view switching period. More specifically, the gantry control circuitry 21 supplies a trigger signal to the counting circuitry 67-n at the switching timing of each view. Along with the supply of the trigger signal, the counting circuitry 67-n adds 1 to the count number stored in the internal memory every time an electrical pulse signal is input from the pulse-height discrimination circuitry 65-n. Along with the supply of the next trigger signal, the counting circuitry 67-n reads out the data of the count number (that is, count data) accumulated in the internal memory, and supplies it to the output circuitry 69. The counting circuitry 67-n also sets again the count number accumulated in the internal memory to the initial value every time a trigger signal is supplied. The counting circuitry 67-n thus counts the electrical pulse signal on a view basis.

The output circuitry 69 is connected to the counting circuitry 67-n as many as the plurality of readout channels included in the X-ray detector 151. For each of the plurality of energy bands, the output circuitry 69 integrates the count data from the counting circuitry 67-n as many as the plurality of readout channels, and generates count data for the plurality of readout channels on a view basis. The count data of each energy band is a set of data of count numbers defined by a channel, a segment (column), and an energy band. The count data of each energy band is transmitted to the console 30 on a view basis. The count data on a view basis is called a count data set.

As described above, the data acquisition circuitry 153-1 shown in FIG. 7 includes the analog pulse-height discrimination circuitry 65-n and the counting circuitry 67-n, which are the same as the components of a conventional data acquisition circuitry. In the data acquisition circuitry 153-1 shown in FIG. 7, the number of counting channels is extended as compared to the conventional data acquisition circuitry. However, the individual components have been field-proven. Although the implementation area and power increase in proportion to the number of counting channels, the circuitry can be implemented.

FIG. 8 is a block diagram showing another example of the arrangement of a data acquisition circuitry 153-2 according to this embodiment. Note that the data acquisition circuitry 153-2 shown in FIG. 8 also includes readout channels as many as channels corresponding to the X-ray detection elements, like the data acquisition circuitry 153-1 shown in FIG. 7. The plurality of readout channels are parallelly implemented on an integrated circuitry such as an ASIC.

FIG. 8 illustrates only the arrangement of the data acquisition circuitry 153-2 corresponding to one readout channel to avoid redundancy.

The data acquisition circuitry 153-2 shown in FIG. 8 includes a preamplifier circuitry 71, a variable gain amplifier circuitry 73, a buffer amplifier circuitry 75, an A/D conversion circuitry (to be referred to as an ADC hereinafter) 77, a digital filter circuitry 79, an integrated counting circuitry 81, and an output circuitry 83.

The preamplifier circuitry 71 amplifies a current signal from the X-ray detection element of a connection destination. More specifically, the preamplifier circuitry 71 converts a current signal from the X-ray detection element of the connection destination into a voltage signal having a voltage value (peak value) proportional to the charge amount of the current signal. The variable gain amplifier circuitry 73 is connected to the preamplifier circuitry 71. The variable gain amplifier circuitry 73 amplifies the voltage signal from the preamplifier circuitry 71 by a variable gain. The gain of the variable gain amplifier circuitry 73 can be set to an arbitrary value by, for example, the user via the input circuitry 39. The buffer amplifier circuitry 75 is connected to the variable gain amplifier circuitry 73. The buffer amplifier circuitry 75 amplifies the voltage signal from the variable gain amplifier circuitry 73 by a gain to suppress a variation in the frequency in the ADC 77 of the subsequent stage. The ADC 77 is connected to the buffer amplifier circuitry 75.

The ADC 77 samples the voltage signal from the buffer amplifier circuitry 75 by a predetermined number of bits, and converts the voltage signal into a discrete time series digital signal having a data value corresponding to the peak value of the voltage signal from the buffer amplifier circuitry 75. The digital filter circuitry 79 is connected to the ADC 77. The digital filter circuitry 79 analyzes the digital signal from the ADC 77, thereby specifying the arrival time of X-ray photons and the energy of the X-ray photons. The arrival time of the X-ray photons corresponds to the time at which the peak is recorded, and the energy of the X-ray photons corresponds to the data value at the peak. A digital signal representing the arrival time of X-ray photons and the energy of the X-ray photons will be referred to as an energy signal hereinafter. The integrated counting circuitry 81 is connected to the digital filter circuitry 79.

The integrated counting circuitry 81 includes counting channels in a number matching the number n of energy bands. Each counting channel includes a discrimination circuitry 811-1, 811-2, 811-3, . . . , 811-n and a counting circuitry 813-1, 813-2, 813-3, . . . , 813-n. Based on an energy signal repetitively supplied from the digital filter circuitry 79, the plurality of discrimination circuitry 811-n discriminate the energy band to which X-ray photons corresponding to the energy signal belong. Different energy thresholds are assigned to the discrimination circuitry 811-n. Each discrimination circuitry 811-n performs threshold processing based on the energy threshold for a repetitively supplied energy signal so as to pass an energy signal belonging to an energy band corresponding to the energy threshold and block an energy signal belonging to an energy band that does not correspond to the energy threshold. Each counting circuitry 813-n counts the energy signal supplied from the discrimination circuitry 811-n of the connection source. The plurality of counting circuitry 813-n count the energy signals from the discrimination circuitry 811-n at a readout period that matches the view switching period. More specifically, the gantry control circuitry 21 supplies a trigger signal to the counting circuitry 813-n at the switching timing of each view. Along with the supply of the trigger signal, the counting circuitry 813-n adds 1 to the count number stored in the internal memory every time an energy signal is input from the discrimination circuitry 811-n. Along with the supply of the next trigger signal, the counting circuitry 813-n reads out the data of the count number (that is, count data) accumulated in the internal memory, and supplies it to the output circuitry 83. The counting circuitry 813-n also sets again the count number accumulated in the internal memory to the initial value every time a trigger signal is supplied. The counting circuitry 813-n thus counts the energy signal on a view basis.

The output circuitry 83 is connected to the integrated counting circuitry 81 corresponding to the plurality of readout channels included in the X-ray detector 151. For each of the plurality of energy bands, the output circuitry 83 integrates the count data from the integrated counting circuitry 81 corresponding to the plurality of readout channels, and generates count data for the plurality of readout channels on a view basis. The count data of each energy band is a set of data of count numbers defined by a channel, a segment (column), and an energy band. The count data of each energy band is transmitted to the console 30 on a view basis. The count data on a view basis is called a count data set.

As described above, in the data acquisition circuitry 153-2 shown in FIG. 8, the ADC 77 is implemented in the ASIC, the output from the ADC 77 is processed by the digital filter circuitry 79, and the output from the digital filter circuitry 79 is output as count data representing an energy spectrum. The X-ray intensity required in CT is as high as 3-600×10$^6$ ph/s/mm$^2$ after passing through the wedge filter ("Enabling Photon Counting Clinical X-ray CT", K. Taguchi, et al. 2009 IEEE Proc. Nucl. Sci. pp. 3581-3585). In the data acquisition circuitry 153-2 shown in FIG. 8, the sampling speed of the ADC 77 is required to be 100 Msps (Sampling Per Second) or more. Hence, there is a fear of heat generation, implementation area, and the like, as in the arrangement shown in FIG. 7. However, an ADC with a speed of 1 Gsps or more is also commercially available, which has a high degree of implementability.

An example of the operation of photon counting CT imaging according to this embodiment will be described next. FIG. 9 is a flowchart showing the typical procedure of photon counting CT imaging performed under the control of the system control circuitry 43.

As shown in FIG. 9, the system control circuitry 43 controls the gantry control circuitry 21 to perform photon counting CT imaging for the subject S and acquire count data concerning a plurality of energy bands (step S1). In step S1, the gantry control circuitry 21 controls the X-ray generation system 13, the X-ray detection system 15, and the rotation driver 19 to execute photon counting CT imaging of the subject S. The rotation driver 19 rotates at a predetermined angular velocity under the control of the gantry control circuitry 21. The high voltage generator 133 of the X-ray generation system 13 applies a high voltage corresponding to a set tube voltage value to the X-ray tube 131 and supplies a filament current to the X-ray tube 131 under the control of the gantry control circuitry 21. The data acquisition circuitry 153 of the X-ray detection system 15 acquires a count data set on a view basis in synchronism with view switching under the control of the gantry control circuitry 21. The count data set is transmitted from the gantry to the console by a transmission apparatus (not shown). The count data set is a set of data in which the energy value of an energy band, a segment number, and a channel number are assigned to each of the plurality of X-ray detection elements. In other words, the count data set represents an energy distribution for the count number of each X-ray detection element.

When step S1 is performed, the system control circuitry 43 causes the reconstruction circuitry 33 to execute the X-ray absorption amount calculation module 335 (step S2). In step S2, the reconstruction circuitry 33 calculates the X-ray absorption amount of each of a plurality of base substances without the influence of a detector response characteristic based on the count data set acquired in step S1, the energy spectrum of incident X-rays on the subject S, and a response function stored in the response function memory circuitry 331. The X-ray absorption amount calculation processing for each base substance is also called substance discrimination.

More specifically, first, the reconstruction circuitry 33 reads out data of the response function from the response function memory circuitry 331. Next, the reconstruction circuitry 33 calculates the difference between the count data set and a model function while changing the X-ray absorption amount of each base substance included in the model function, and decides the final X-ray absorption amount of each base substance with which the calculated difference becomes smaller than a threshold. At this time, the reconstruction circuitry 33 decides the final X-ray absorption amount with which the difference becomes smaller than the threshold simultaneously for all of the plurality of energy bands. As described above, the model function is defined by convolution of the response function for an integrated value of the energy spectrum of incident X-rays on the subject S and a power of a Napier's constant e using the X-ray absorption amount as an exponent. The energy spectrum of the incident X-rays on the subject S is measured by the X-ray detection system 15 at the time of, for example, calibration, and stored in the response function memory circuitry 331, the main memory circuitry 41, or the like. A threshold $\varepsilon$ is decided to an arbitrary value in advance. For example, if there are two types of base substances, that is, the base substances 0 and the base substance 1, the reconstruction circuitry 33 decides the final X-ray absorption amount on a view basis in accordance with the following procedure.

First, an initial value $\mu_{01}$ of an X-ray attenuation coefficient and an initial value $L_{01}$ of a transmission path length for the base substance 0 and an initial value $\mu_{11}$ of an X-ray attenuation coefficient and an initial value $L_{11}$ of a transmission path length for the base substance 1 are set automatically or according to an instruction input by the user via the input circuitry 39. The initial value $\mu_{01}$ of the X-ray attenuation coefficient and the initial value $L_{01}$ of the transmission path length and the initial value $\mu_{11}$ of the X-ray attenuation coefficient and the initial value $L_{11}$ of the transmission path length are set in advance based on experimental or statistical knowledge. As indicated by expressions (4) below, the reconstruction circuitry 33 calculates the difference (left-hand side of expression (4)) between the count data set $I_{det}(E)$ and an initial model function $M_0(E)$, and compares the difference with the threshold $\varepsilon$.

$$\Sigma_{bini}{}^j \{I_{det(E)} - M_0(E) \le \varepsilon\} \qquad (4)$$

$$M_0(E) = \{I_0(E)\exp(-\mu_{01}(E)L_{01} - \mu_{11}(E)L_{11})\} \otimes R(E)$$

As indicated by expressions (4), the reconstruction circuitry 33 performs the comparison of the difference and the threshold for all energy bands i. Upon determining for all of the plurality of energy bands that the difference is smaller than the threshold $\varepsilon$, the initial value $\mu_{01}$ of the X-ray attenuation coefficient and the initial value $L_{01}$ of the transmission path length for the base substance 0 and the initial value $\mu_{11}$ of the X-ray attenuation coefficient and the initial value $L_{11}$ of the transmission path length for the base substance 1 are decided as final values. The final X-ray attenuation coefficient and transmission path length are stored in the count data memory circuitry 31 for each base substance.

On the other hand, upon determining for at least one of the plurality of energy bands that the difference is larger than the threshold $\varepsilon$, the X-ray attenuation coefficient and the transmission path length for the base substance 0 and the X-ray attenuation coefficient and the transmission path length for the base substance 1 are changed. The X-ray attenuation coefficients and the transmission path lengths are changed by an existing method. As indicated by expressions (5) below, the difference (left-hand side of expression (5)) between the count data set and a model function $M_n(E)$ after the nth iteration is calculated and compared with the threshold $\varepsilon$.

$$\Sigma_{bini}{}^j \{I_{det}(E) - M_n(E) \le \varepsilon\} \qquad (5)$$

$$M_n(E) = \{I_0(E)\exp(-\mu_{0n}(E)L_{0n} - \mu_{1n}(E)L_{1n})\} \otimes R(E)$$

In the above equations n indicates the nth iteration. Note that the initial value is n=0.

In this way, the difference (left-hand side of expression (5)) between the count data set and the model function $M_n(E)$ is iteratively calculated until the difference between the count data set and the model function $M_n(E)$ falls below the threshold $\varepsilon$ for all of the plurality of energy bands.

Upon determining for all of the plurality of energy bands that the difference between the count data set and the model function $M_n(E)$ falls below the threshold $\varepsilon$, an X-ray attenuation coefficient $\mu_{0n}$ and a transmission path length $L_{0n}$ for the base substance 0 and an X-ray attenuation coefficient $\mu_{1n}$ and a transmission path length $L_{1n}$ for the base substance 1 included in the model function $M_n(E)$ are decided as final values. The final X-ray attenuation coefficient and transmission path length are stored in the count data memory circuitry 31 for each base substance.

Note that the above-described method of calculating the X-ray attenuation coefficient and transmission path length for a base substance is merely an example, and the X-ray attenuation coefficient and transmission path length for a base substance can be calculated by any calculation method. For example, the difference between inverse convolution of the count data set by the response function and the integrated value of the energy spectrum of incident X-ray energy and a power of the Napier's constant using the X-ray absorption amount as an exponent may be compared with the threshold.

In the above-described method, the threshold $\varepsilon$ is set in advance, and the model function $M_n(E)$ when the difference between the count data set and the model function $M_n(E)$ falls below the threshold $\varepsilon$ is decided as the final model function. However, the embodiment is not limited to this. For example, the difference between the count data set and the model function $M_n(E)$ is calculated a plurality of times, that is, m times, and out of m model functions $M_m(E)$, a model function $M(E)$ when the difference is a local minimum is decided as the final model function.

In addition, the X-ray absorption amount with which the difference between the count data set and the model function becomes smaller than the threshold $\varepsilon$ simultaneously for all of the plurality of energy bands is decided as the final X-ray absorption amount. However, the embodiment is not limited to this. For example, an X-ray absorption amount with which the difference becomes smaller than the threshold ε for a predetermined number of energy bands out of the plurality of energy bands may be decided as the final X-ray absorption amount.

When step S2 is performed, the system control circuitry 43 causes the reconstruction circuitry 33 to perform reconstruction processing (step S3). In step S3, based on the X-ray absorption amount of each of the plurality of base substances calculated in step S2, the reconstruction circuitry 33 reconstructs a photon counting CT image that expresses the spatial distribution of the base substance included in the subject S. The type of the base substance to be used for the reconstruction can arbitrarily be selected from the plurality of base substances whose X-ray absorption amounts are calculated in step S2. For example, a photon counting CT image reconstructed based on the X-ray absorption amount of the base substance 0 expresses the spatial distribution of the base substance 0. A photon counting CT image reconstructed based on the X-ray absorption amount of the base substance 1 expresses the spatial distribution of the base substance 1. Note that as the image reconstruction algorithm, an existing image reconstruction algorithm such as an analytic image reconstruction method based on FBP (Filtered Back Projection) or CBP (Convolution Back Projection) or a statistical image reconstruction method based on ML-EM (Maximum Likelihood Expectation Maximization), OS-EM (Ordered Subset Expectation Maximization), or OS-SART (Ordered Subset Simultaneous Algebraic Reconstruction Techniques) is used. A k-edge imaging method may be incorporated in the image reconstruction algorithm. Plainly speaking, k-edge imaging is a method of reconstructing a photon counting CT image expressing the spatial distribution of an imaging target substance based on count data concerning energy bands on both sides of an energy band to which the k-edge of the imaging target substance belongs.

When step S3 is performed, the system control circuitry 43 causes the display circuitry 37 to perform display processing (step S4). In step S4, the display circuitry 37 displays the photon counting CT image reconstructed in step S3.

The description of an example of the operation of photon counting CT imaging according to this embodiment will be ended here.

As described above, the photon counting CT apparatus according to this embodiment includes the X-ray generation system 13, the X-ray detection system 15, the response function memory circuitry 331, and the reconstruction circuitry 33. The X-ray generation system 13 generates X-rays. The X-ray detection system 15 includes the X-ray detector 151 that detects the X-rays generated by the X-ray generation system 13 and transmitted through the subject S, and the data acquisition circuitry 153 that acquires count data concerning the count number of X-rays detected based on the output signal from the X-ray detector 151 for a plurality of energy bands. The response function memory circuitry 331 stores data of a response function that associates incident X-rays on the X-ray detection system 15 with a detector response characteristic. By executing the X-ray absorption amount calculation module 335, the reconstruction circuitry 33 calculates the X-ray absorption amount of each of a plurality of base substances based on count data concerning a plurality of energy bands, the energy spectrum of incident X-rays generated by the X-ray generation system 13, and the response function readout from the response function memory circuitry 331.

As described above, in this embodiment, the X-ray absorption amount of each base substance is decided in consideration of the response function representing the detector response characteristic. Hence, the decided X-ray absorption amount is not affected by the detector response characteristic, and its accuracy improves as compared to an X-ray absorption amount calculated without considering the detector response characteristic. The response function according to this embodiment expresses not only a main peak but also an escape peak or the energy of the k-characteristic X-rays of a scintillator material. This makes it possible to more accurately calculate the X-ray absorption amount of a base substance. Hence, the accuracy of a photon counting CT image reconstructed based on the X-ray absorption amount also improves.

Thus, according to this embodiment, even a detector having a low energy resolving power can accurately discriminate a substance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A photon counting apparatus, comprising:
an X-ray tube configured to generate X-rays;
an X-ray detector configured to detect the X-rays generated by the X-ray tube and transmitted through a subject;
data acquisition circuitry configured to acquire count data concerning a count number of the detected X-rays for a plurality of energy bands, based on an output signal from the X-ray detector;
memory circuitry configured to store data of a response function that associates an energy of incident X-rays on the X-ray detector with a response characteristic of a system including at least one of the X-ray detector and the data acquisition circuitry; and
processing circuitry configured to calculate an X-ray absorption amount of each of a plurality of base substances based on the count data concerning the plurality of energy bands acquired by the data acquisition circuitry, an energy spectrum of the incident X-rays generated by the X-ray tube, and the data of the response function stored in the memory circuitry.

2. The photon counting apparatus according to claim 1, where the processing circuitry is further configured to reconstruct an image based on the X-ray absorption amount of each of the plurality of base substances.

3. The photon counting apparatus according to claim 1, where the processing circuitry is further configured to calculate a difference between the count data and a model function representing an energy spectrum of X-rays transmitted through the subject while changing an X-ray absorption amount of each of the plurality of base substances included in the model function that describes the response characteristic of the system, and decide a final X-ray absorption amount of each of the plurality of base substances with which the difference becomes smaller than a predetermined value.

4. The photon counting apparatus according to claim 3, where the model function is defined by convolution of the response function for an integrated value of the energy spectrum of the incident X-rays generated by the X-ray tube and a power of a Napier's constant using the X-ray absorption amount as an exponent.

5. The photon counting apparatus according to claim 3, where the X-ray absorption amount of each of the plurality of base substances is defined by a product of an X-ray attenuation coefficient and a transmission path length of each of the plurality of base substances.

6. The photon counting apparatus according to claim 3, where the processing circuitry is further configured to decide the final X-ray absorption amount with which the difference becomes smaller than the predetermined value simultaneously for all of the plurality of energy bands.

7. The photon counting apparatus according to claim 3, where the processing circuitry is further configured to decide the final X-ray absorption amount on a view basis.

8. The photon counting apparatus according to claim 1, further comprising an X-ray filter configured to attenuate the X-rays generated by the X-ray tube,
wherein the energy spectrum of the incident X-rays generated by the X-ray tube is an energy spectrum of X-rays that enter the subject through the X-ray filter.

9. The photon counting apparatus according to claim 1, wherein the response function defines a relationship between detection energy and an output response for each energy of the X-rays.

10. The photon counting apparatus according to claim 9, wherein the response function expresses a main peak corresponding to the energy of the X-rays from the X-ray tube.

11. The photon counting apparatus according to claim 10, wherein
the X-ray tube includes an anode target, and
the response function expresses the main peak, characteristic X-rays originated from the anode target of the X-ray tube, and an escape peak corresponding to energy lower than the energy of the X-rays from the X-ray tube by the energy of the characteristic X-rays.

12. The photon counting apparatus according to claim 1, wherein the processing circuitry is further configured to generate the response function in advance based on an output of the X-ray detector for each of a plurality of monochromatic X-rays.

13. The photon counting apparatus according to claim 1, wherein the plurality of energy bands comprise at least 16 energy bands, and
the data acquisition circuitry is further configured to acquire the count data for the at least 16 energy bands.

14. The photon counting apparatus according to claim 1, wherein the data acquisition circuitry further comprises:
discrimination circuitry configured to discriminate an analog output signal from the X-ray detector to the plurality of energy bands based on a peak value of the analog output signal from the X-ray detector; and
counting circuitry configured to generate the count data for the plurality of energy bands based on an output signal from the discrimination circuitry.

15. The photon counting apparatus according to claim 1, wherein the data acquisition circuitry further comprises:
conversion circuitry configured to convert an analog output signal from the X-ray detector into a digital signal;
discrimination circuitry configured to discriminate the digital signal from the conversion circuitry to the plurality of energy bands based on a data value of the digital signal from the conversion circuitry; and
counting circuitry configured to generate the count data for the plurality of energy bands based on an output signal from the discrimination circuitry.

16. The photon counting apparatus according to claim 1, wherein the X-ray detector further comprises a phosphor configured to convert X-rays into fluorescence, and a photodetector configured to convert the fluorescence into an output signal.

17. The photon counting apparatus according to claim 1, wherein the X-ray detector further comprises a semiconductor configured to convert X-rays into electron-hole pairs, and electrodes provided at two ends of the semiconductor and configured to convert the electron-hole pairs into an output signal.

18. The photon counting apparatus according to claim 1, wherein the memory circuitry stores the data of the response function that associates energy of incident X-rays on the X-ray detector with a response characteristic of both of the X-ray detector and the data acquisition circuitry.

19. An image generating apparatus, comprising:
memory circuitry configured to store data of a response function that associates energy of incident X rays on an X ray detector with a response characteristic of a system including at least one of the X ray detector and data acquisition circuitry; and
processing circuitry configured to
acquire count data concerning a count number of X rays for a plurality of energy bands; and
calculate an X ray absorption amount of each of a plurality of base substances based on the count data concerning the plurality of energy bands acquired by the data acquisition circuitry, an energy spectrum of the incident X rays generated by an X ray tube, and the data of the response function stored in the memory circuitry.

* * * * *